United States Patent
Auvray et al.

(10) Patent No.: US 10,271,808 B2
(45) Date of Patent: Apr. 30, 2019

(54) AUTOMATIC POSITIONING OF ABSORPTION MEANS IN X-RAY IMAGE ACQUISITION

(75) Inventors: Vincent Maurice Andre Auvray, Paris (FR); Raoul Florent, Ville d'Avray (FR); Willem Frederik Den Hartog, Eindhoven (NL); Peter Willem Van Den Houten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 408 days.

(21) Appl. No.: 13/636,454

(22) PCT Filed: Mar. 24, 2011

(86) PCT No.: PCT/IB2011/051255
§ 371 (c)(1),
(2), (4) Date: Sep. 21, 2012

(87) PCT Pub. No.: WO2011/121502
PCT Pub. Date: Oct. 6, 2011

(65) Prior Publication Data
US 2013/0028384 A1 Jan. 31, 2013

(30) Foreign Application Priority Data
Mar. 31, 2010 (EP) .................... 10305332

(51) Int. Cl.
*A61B 6/06* (2006.01)
*A61B 6/00* (2006.01)
*A61B 6/03* (2006.01)

(52) U.S. Cl.
CPC .............. *A61B 6/481* (2013.01); *A61B 6/032* (2013.01); *A61B 6/06* (2013.01); *A61B 6/4035* (2013.01);
(Continued)

(58) Field of Classification Search
CPC ......... A61B 6/032; A61B 6/4035; A61B 6/06; A61B 6/469; G21K 1/10; G21K 1/02
(Continued)

(56) References Cited

U.S. PATENT DOCUMENTS 3,631,249 A 12/1971 Friede et al.
4,287,296 A 9/1981 Vanassche et al.
(Continued)

FOREIGN PATENT DOCUMENTS

JP H08103436 A 4/1996
JP 2004089699 A 3/2004
(Continued)

OTHER PUBLICATIONS

"X-Ray Production and Angiography Equipment, Lecture 4", Radiation Protection in Cardiology, International Atomic Energy Agency, 2010.

*Primary Examiner* — Michael Maskell (57) ABSTRACT

The present invention relates to automatic absorption means positioning in X-ray image acquisition. To improve image quality and to optimize the radiation exposure of an object, optimal position for X-ray absorption means is provided. A first sequence (113) of X-ray images is acquired (112). For each of the images, the optimal position (115) for X-ray absorption means is determined (114). A second sequence (117) of X-ray images is associated 10 (116) with corresponding images of the first sequence. The determined optimal position for the absorption means (14) of the associated corresponding images of the first sequence (113) is selected for an acquisition of the second sequence (117). Hence, a situation-specific database with optimized positions for the absorption means is generated on behalf of the
(Continued)

first sequence in order to provide the generated position information for the actual acquisition of a 15 second sequence of images.

20 Claims, 6 Drawing Sheets (52) U.S. Cl.
CPC .............. *A61B 6/488* (2013.01); *A61B 6/504* (2013.01); *A61B 6/5235* (2013.01); *A61B 6/542* (2013.01); *A61B 6/4441* (2013.01); *A61B 6/583* (2013.01)

(58) Field of Classification Search
USPC .................................. 378/205, 203, 150, 151
See application file for complete search history.

(56) References Cited

U.S. PATENT DOCUMENTS

| | | | |
|---|---|---|---|
| 4,400,827 A | 8/1983 | Spears | |
| 4,448,200 A * | 5/1984 | Brooks | A61B 6/481 378/151 |
| 5,287,396 A | 2/1994 | Stegehuis | |
| 6,055,295 A * | 4/2000 | Murthy | A61B 6/06 378/145 |
| 6,215,853 B1 * | 4/2001 | Kump | A61B 6/06 378/147 |
| 6,377,656 B1 | 4/2002 | Ueki et al. | |
| 7,289,652 B2 * | 10/2007 | Florent | G06T 7/74 382/130 |
| 2008/0037708 A1 | 2/2008 | Kuzmanovic | |
| 2012/0250828 A1 * | 10/2012 | Takahashi | A61B 6/06 378/150 |

FOREIGN PATENT DOCUMENTS

| | | | |
|---|---|---|---|
| WO | WO2005009243 | 2/2005 | |
| WO | WO 2005009243 A1 * | 2/2005 | .............. A61B 6/06 |
| WO | WO2009063353 | 5/2009 | |
| WO | WO 2009063353 A3 * | 7/2009 | .............. A61B 6/032 |

* cited by examiner

AUTOMATIC POSITIONING OF ABSORPTION MEANS IN X-RAY IMAGE ACQUISITION

FIELD OF THE INVENTION

The present invention relates to automatic absorption means positioning in X-ray image acquisition. The invention particularly relates to a device for automatic absorption means positioning, a medical imaging system, and a method for automatic absorption means positioning, as well as to a computer program element and a computer readable medium.

BACKGROUND OF THE INVENTION

To limit the region exposed to the X-ray beam in X-ray examination apparatuses, absorption means are used, being arranged between the X-ray source and the X-ray detector. For example, to limit the radiation to parts of the anatomy, clinicians position shutters to delimit the region of interest. In addition to shutters completely hiding the covered region, wedges are described in U.S. Pat. No. 3,631,249. This document describes a diaphragm with plates shaped as wedges producing a half shade effect compared to a primary ray diaphragm. However, positioning of absorption means is time consuming, especially when performed manually. As a result, inaccuracy or even no use at all may reduce the image quality and may also increase the total radiation exposure dose.

SUMMARY OF THE INVENTION

It is an object of the present invention to improve image quality and to further optimize the radiation exposure of an object.

The object of the present invention is solved by the subject-matter of the independent claims, wherein further embodiments are incorporated in the dependent claims.

It should be noted that the following described aspects of the invention apply also for the method, the program element, the computer readable medium, the device and the medical imaging system.

According to an aspect of the invention, a device for automatic absorption means positioning in X-ray image acquisition is provided. The device comprises a processing unit, which is adapted to receive image data of images of a first sequence of X-ray images of an object; to determine optimal position for X-ray absorption means for each of the images of the first sequence of images; to associate images of a second sequence of X-ray images with corresponding images of the first sequence of X-ray images; and to select the determined optimal position for X-ray absorption means of the associated corresponding images of the first sequence of X-ray images for an acquisition of the second sequence of X-ray images.

According to another aspect of the invention, a medical imaging system is provided, comprising X-ray image acquisition means, X-ray absorption means, and a device according to the exemplary embodiment described above. The acquisition means comprise at least one X-ray source and at least one X-ray detector. The acquisition means are adapted to acquire image data of images of a first sequence of X-ray images of an object and to acquire image data of images of a second sequence of X-ray images of an object. The X-ray absorption means are arranged between the at least one X-ray source and the at least one X-ray detector such that an object can be placed at least partially between the X-ray absorption means and the at least one X-ray detector. Further, actuating means are provided to position the X-ray absorption means. The processing unit activates the actuating means according to the determined optimal position for the acquisition of the image data of the images of the second sequence of X-ray images, which determined optimal position is provided by the processing unit of the device for automatic absorption means positioning.

According to another aspect of the invention, there is provided a method for automatic absorption means positioning in X-ray image acquisition, comprising the following steps: a) acquiring image data of images of a first sequence of X-ray images of an object; b) determining optimal position for X-ray absorption means for each of the images of the first sequence of images; c) associating images of a second sequence of X-ray images with corresponding images of the first sequence of X-ray images; and d) selecting the determined optimal position for the X-ray absorption means of the associated corresponding images of the first sequence of X-ray images for an acquisition of the second sequence of X-ray images.

The term "images of a sequence" relates to a plurality of setting for sequential exposures. The term "image data" relates to image information provided by acquisition or exposure of the image. In other words, the term "image" relates to the parameters describing respectively defining certain parameters for the acquisition of the image data. The image data itself describes the so to speak image content. In other words, the term "image" can describe both an already acquired image as well as an image which is designated to be acquired.

For example, the optimal positions for the X-ray absorption means are determined such that they cover as much image area as possible by leaving image area according to a predetermined criterion uncovered. The criterion can be determined by a user, for example, the criterion can relate to certain areas showing specific features that are of particular interest for the user.

According to an exemplary embodiment, the first sequence of X-ray images can be achieved by acquiring more than one sequence of the first type. For example, images of several sequences can be selected to form the so-called first sequence for further steps. As another example, images can be averaged or overlaid to receive the first sequence as a result.

According to an exemplary embodiment, the images of the first sequence of X-ray images and the images of the second sequence of X-ray images are acquired according to at least one different image acquisition parameter.

For example, the images of the first sequence of X-ray images are acquired with a higher image contrast than the images of the second sequence of X-ray images.

For example, a higher contrast can be achieved by a contrast agent in the region of interest.

According to an exemplary embodiment, the contrast agent dose in the first sequence is higher than in the second sequence.

For example, the images of the first sequence of X-ray images are angiograms, and the images of the second sequence of X-ray images are fluoroscopy images.

According to a further exemplary embodiment, step c) comprises aligning the corresponding images of the first sequence of X-ray images with the associated images of a second sequence of X-ray images and adjusting the selected optimal positions according to the respective alignment.

It can be seen as the gist of the invention to generate a situation-specific database with optimized absorption means positions for the respective images of a sequence of X-ray images. By generating this position information database, it is possible to provide the generated position information for a second sequence of images. Thereby, the second sequence can be performed such that the image quality and also the aspect of radiation dose to the object, for example a patient, can be improved. For example, during the second sequence, only those portions or regions of the respective images are exposed to X-ray radiation which have been selected according to step b) of determining optimal position for X-ray absorption means. As an example, X-ray absorption means can also be optimally positioned even if the image data acquired during the second sequence of X-ray images does not show enough image information to define the region of interest which would be necessary for determining optimal position. But since the determining of the optimal position has been performed for the first sequence of images and due to the associating step or the step when corresponding images are associated with each other, so to speak the determined positions are transformed from the first sequence to the second sequence.

In other words, a situation-specific database with optimized positions for the absorption means is generated on behalf of the first sequence in order to provide the generated position information for the actual acquisition of a second sequence of images.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

According to the present invention, an automatic absorption means positioning will be described in the following which positioning is patient-specific thus providing more accurate positioning compared to generic default positions for the positioning of absorption means.

Before relating to the drawings, a short discussion of some aspects of the invention follows. To set optimal absorption means positions corresponding to a certain sequence of images, i.e. a second sequence of images, the invention proposes to associate the second sequence of images with a first sequence of images. An absorption means position compatible with the first sequence is assumed to be equally suited to the second sequence of images.

As an example, in cathlab workflow, a fluoroscopic run, as a second sequence of images, is usually preceded by an angiography of the considered branch under the same angulation, wherein the angiography means a first sequence of images. This is because the clinician needs to visualize the vasculature in which he will navigate and practice his intervention. In this view, the anatomy of interest can indeed be visualized since the coronaries that will be treated are injected with contrast agent making them visible.

Figure 1:
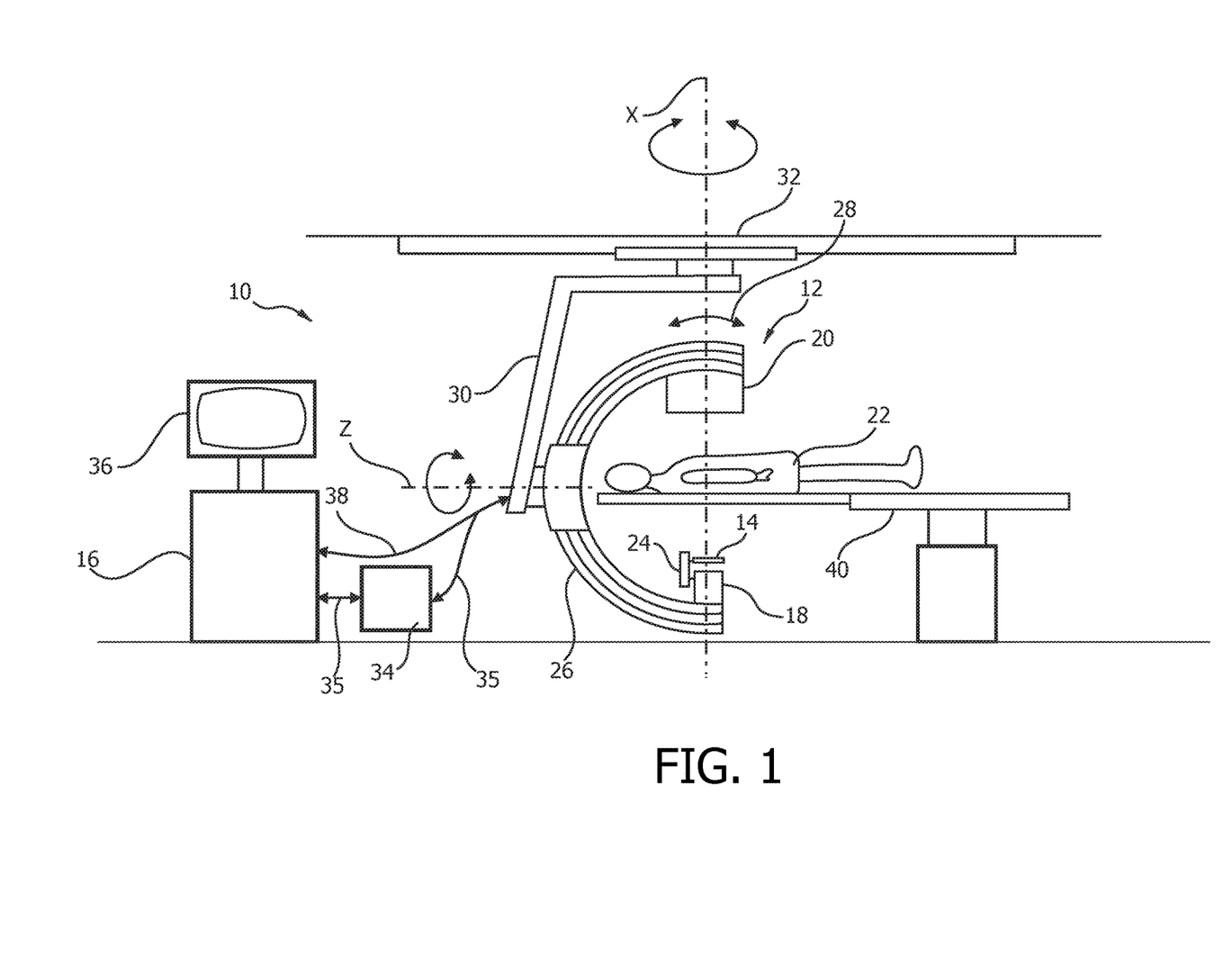
FIG. 1 illustrates an X-ray imaging system according to an exemplary embodiment of the invention.

FIG. 1 schematically shows a medical imaging system 10 comprising X-ray image acquisition means 12, X-ray absorption means 14, and a device 16 for automatic absorption means positioning in X-ray image acquisition.

The X-ray absorption means 14 are adapted to absorb X-ray radiation from the X-ray source 18. For example, the X-ray absorption means comprise an X-ray diaphragm or several X-ray diaphragms. According to another example, the X-ray absorption means 14 comprise one or several wedges (also not shown). According to another example, the absorption means 14 can comprise shutters. Of course, the absorption means 14 can comprise a combination of the afore-mentioned examples.

The device 16 comprises a processing unit (not shown).

The X-ray image acquisition means 12 comprise at least one X-ray source 18 and at least one X-ray detector 20. The image acquisition means 12 are adapted to acquire image data of images of a first sequence of X-ray images of an object, for example a patient 22, and acquire image data of images of a second sequence of X-ray images of the object.

The X-ray absorption means 14 are arranged between the X-ray source 18 and the X-ray detector 20 such that the object, for example the patient, can be placed at least partially between the X-ray absorption means 14 and the X-ray detector 20. Further, actuating means 24 are provided to position the X-ray absorption means 14.

The processing unit is adapted to receive image data of images of a first sequence of X-ray images of the object. The processing unit is further adapted to determine optimal position for the X-ray absorption means 14 for each of the images of the first sequence of images. The processing unit is further adapted to associate images of a second sequence of X-ray images with corresponding images of the first sequence of X-ray images. The processing unit is also adapted to select the determined optimal position for the X-ray absorption means 14 of the associated corresponding images of the first sequence of X-ray images for an acquisition of the second sequence of X-ray images.

The processing unit further activates the actuating means 24 according to the determined optimal position of the X-ray absorption means for the acquisition of the image data of the images of the second sequence of X-ray images.

The medical imaging system 10 is shown as a so-called C-type X-ray image acquisition device where the X-ray source 18 and detection module or detector 20 are arranged on opposing ends of a C-arm 26. The C-arm is rotatably mounted around a horizontal axis indicated as Z-axis. The C-arm can further be rotated in a circular or semi-circular form indicated by arrow 28. Further, according to the example shown, the C-arm 26 is mounted to a support 30 suspended from a ceiling 32, wherein the support is rotatable around a vertical axis indicated as X-axis. Thus, X-ray images can be acquired from different directions of different regions of interest of the patient 22.

An interface device 34 is arranged to input information by the user, connected to the image acquisition device 12 and the device 16 for automatic absorption means, which connection is provided, for example, by a cable connection 35. Further, a display 36 is provided connected to the device 16. The device 16 is connected to the X-ray image acquisition means 12 and the X-ray absorption means 14 by a cable connection 38. Of course, the connection can also be provided in form of a wireless connection (not shown).

A table 40 is provided to receive a subject to be examined, such as a patient 22. Of course, the table 40 can be adjustable respectively moveable in height and translatable in horizontal direction.

It is noted that the example is shown as a C-type X-ray image acquisition device, although the invention also relates to other types of X-ray image acquisition devices, such as CT systems. Of course, as an X-ray acquisition device, a much more simplified C-arm device or other device can be used than the one shown in FIG. 1.

The table 40 and the X-ray acquisition means 12 are arranged such that during a radiation procedure, the subject or a patient 22 is located between the source of X-ray radiation 18 and the detector 20. The latter is sending data to the device 16 or processing unit, respectively.

Figure 2:
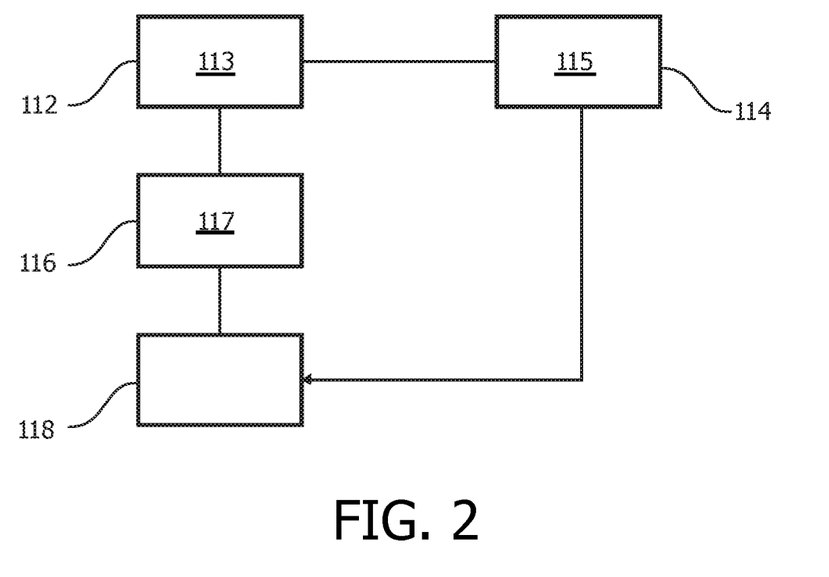
FIG. 2 illustrates the basic steps of a method according to an exemplary embodiment of the invention.

In the following, the basic steps of the method according to the invention shall be described in an example with reference to FIG. 2.

First, in an acquisition step 112, image data of images of a first sequence 113 of X-ray images of an object are acquired. With reference to FIG. 1, this acquisition can be performed by the X-ray image acquisition means 12.

According to an exemplary embodiment, not further shown, the first sequence of X-ray images can be achieved by acquiring more than one sequence of the first type. For example, images can be selected to form the first sequence for further steps. As another example, images can be averaged or overlaid to receive the first sequence as a result.

Next, in a determining step 114, optimal position 115 for X-ray absorption means 14 for each of the images of the first sequence 113 of images is determined.

Then, in an association step 116, images of a second sequence 117 of X-ray images are associated with corresponding images of the first sequence of X-ray images.

In another example, not shown, a series of first sequences 113 is acquired and the association step comprises to associate the series of first sequences with corresponding images of an appropriately selected first sequence.

Further, with reference to FIG. 2 again, in a selection step 118, the determined optimal position 115 for the X-ray absorption means 14 of the associated corresponding images of the first sequence 113 of X-ray images for an acquisition of the second sequence of X-ray images is selected.

The association of the second sequence 117 to the relevant first sequence 113 of images and the selection of the optimal absorption means positions computed for the first sequence of images has the effect that when acquiring the first and second sequence of images with a different phantom, absorption means positions corresponding to the first phantom would apply to a second phantom. Of course, if the first sequence of images is acquired with the same image parameters as the second sequence of images, for example with the same contrast, for example with no contrast, the absorption means would cover a very large or even too large area of the second sequence images, of course depending on the preset parameters, on which the image analysis is based on.

In other words, on behalf of the acquired first sequence of X-ray images, a plurality of optimal position data is achieved by associating images of a second sequence to the images of the first sequence, thus being able to select the determined optimal positions which have been determined for the first sequence of X-ray images.

According to an exemplary embodiment, it is provided that there is no need that the second sequence of images must be actually acquired when selecting the determined optimal positions. For example, if the respective settings for the sequential exposures of the second sequence are known by at least one image parameter, this parameter can then be used for the association or corresponding step, where a connection so to speak is established between the first sequence of images and the second sequence of images. Thus, the optimized positions of X-ray absorption means 14 can then be applied when actually performing the acquisition of the second sequence.

According to an exemplary embodiment, a first image of the second sequence is acquired for receiving at least one parameter on behalf of which the association can be performed. Once the corresponding images of the first sequence are associated with those of the second sequence, which second sequence has not been acquired completely yet, the optimal positions computed for the images of the first sequence can be selected for acquiring the images of the planned second sequence.

Figure 3:
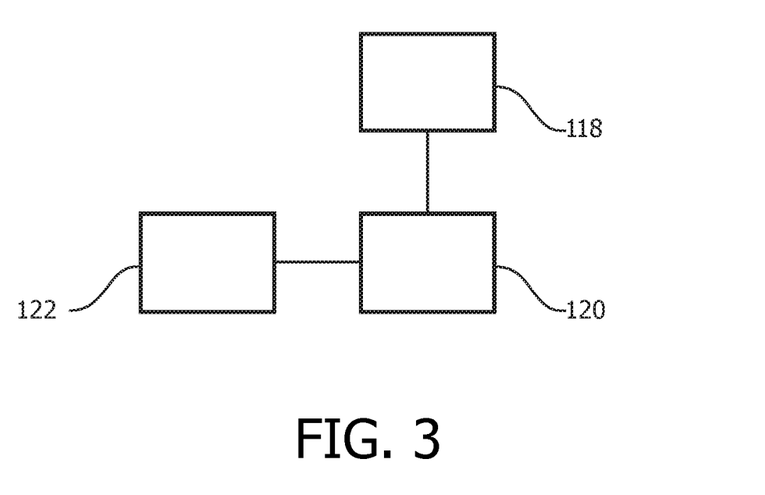
FIG. 3 shows further steps of a method according to another exemplary embodiment.

This is shown in FIG. 3. Following step d) of selecting 118 the determined optimal position, in a following acquisition step 120, the second sequence of X-ray images is acquired. During this acquisition 120 of a second sequence of X-ray images, the X-ray absorption means 14 are positioned 122 according to the selected determined optimal positions derived in step d).

As already mentioned in the introduction, the term "images of a sequence" relates to a plurality of settings for sequential exposures. The term "image data" relates to the image information provided by acquisition or exposure of the image.

The optimal positions for the X-ray absorption means 14 are determined, for example, in such a way, that an area according to a predetermined criterion is left uncovered, whereas as much area as possible outside this area is covered, that is not exposed to X-ray radiation.

According to a further example, the absorption means 14 are arranged such that they provide a range of increasing absorption ratio such that a so to speak transition from zero absorption to complete absorption is provided in a border area at least partially surrounding the area of interest. This may enhance the visual perception by the user who is provided with at least basic additional information about the adjacent area of the region of interest.

According to an example, although not shown, the determining step 114, also referred to as step b), comprises analyzing the image content of the image of the first sequence of X-ray images. For example, the images of the first sequence of X-ray images may comprise a vessel structure, such as a vascular structure.

According to an exemplary embodiment, the vessel structure is a coronary vessel structure. The step of analyzing the image content, for example, may comprise analyzing certain vessel structure features which, for example, may have been preselected by the user.

According to an exemplary embodiment, the images of the first sequence of X-ray images and the images of the second sequence of X-ray images are acquired according to at least one different image acquisition parameters.

For example, the at least one image acquisition parameter comprises image contrast. The images of the first sequence of X-ray images can be acquired with higher image contrast than the images of the second sequence of X-ray images.

For example, the images of the first sequence of X-ray images can be acquired with contrast agent in the region of interest. As an example, the contrast agent is temporarily brought into the region of interest for the purpose of the images of the first sequence.

For example, the images of the first sequence of X-ray images are acquired as angiograms, and the images of the second sequence of X-ray images are fluoroscopy images.

According to a further exemplary embodiment, the angiograms are acquired in a contrast-filled state of the vessels.

According to an exemplary embodiment, the angiograms are vascular angiograms. For example, the vascular angiograms show coronary tree structures.

Figure 4:
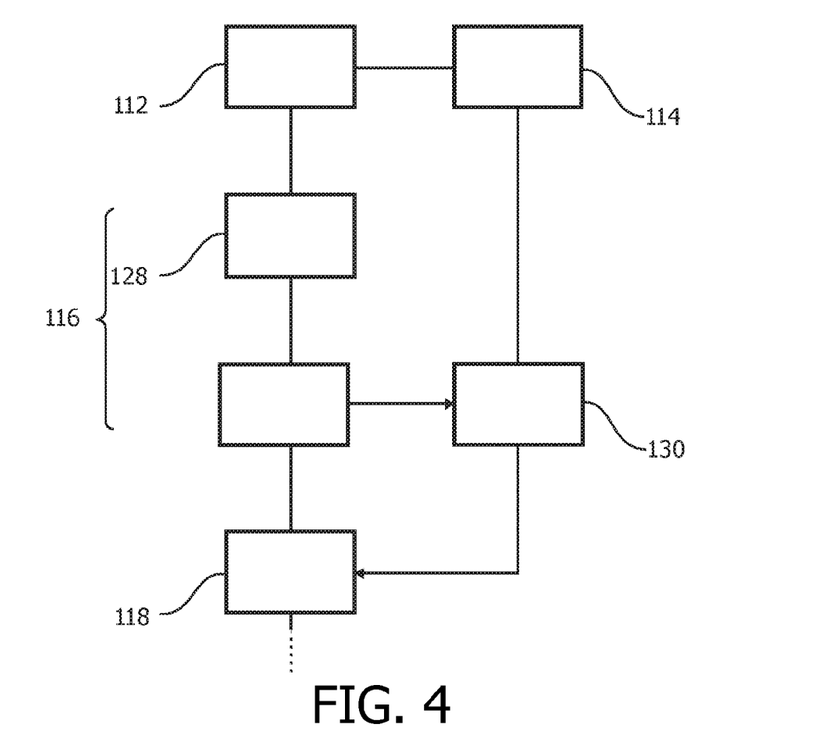
FIG. 4 shows further steps of a further exemplary embodiment of the invention.

According to another exemplary embodiment, shown in FIG. 4, the step c), i.e. is the association step 116 comprises spatially aligning 128 the corresponding images of the first sequence of X-ray images with the associated images of a second sequence of X-ray images, wherein the selected optimal positions are adjusted in an adjusting step 130, according to the respective alignment detected in step c).

For example, for the alignment, system information is used to account for possible modifications of the relative position of the imaging system and the object, such as a patient, between the acquisition of the images of the first sequence of X-ray images and the acquisition of the second sequence of X-ray images.

For example, the selected positions are compensated for translational motion and zooming for the images of the second sequence of X-ray images.

As a further example, the system information comprises position of a table on which the object can be examined. Further, the system information may comprise a selected field of view. As a further example for system information, the distance between the object and the detector can be provided.

According to a further exemplary embodiment, association data is attached to each of the images of the first sequence and to each of the images of the second sequence of X-ray images. This is for associating the images of the second sequence of X-ray images with corresponding images of the first sequence of X-ray images.

For example, the association data comprises imaging angulation data from the X-ray image acquisition means.

The association data may also comprise image type information, such as the type of vasculature or vascular structure.

For example, the type of vasculature is given by the user. According to a further aspect of the invention, the type of vasculature can also be computed automatically from the image.

As a further example, the association data comprises system information of the X-ray acquisition arrangement.

According to a further aspect of the invention, as an example, the images of the first sequence of X-ray images and/or the images of the second sequence of X-ray images are acquired for generating 3D image data. In other words, the images of the respective sequences are taken from different angles with respect to the object, such providing image data from different angles which can then be used for creating 3D model or volume information.

Figure 5:
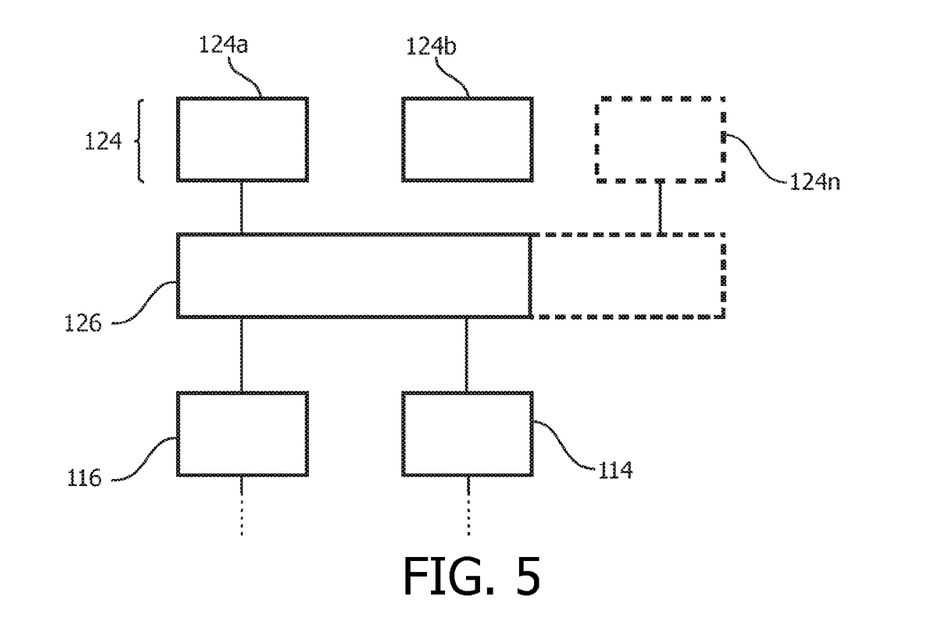
FIG. 5 shows further steps of a further exemplary embodiment of the invention.

According to a further exemplary embodiment, shown in FIG. 5, at least two pre-sequences 124*a*, 124*b* of X-ray images are acquired in an acquisition step 124, and in a selection step 126, the images for the first sequence of images are selected from the at least two pre-sequences of X-ray images, thus providing the first sequence of images as in the acquisition step 112. As indicated with dashed lines and reference number 124*n*, more than two sequences, i.e. n sequences can be acquired for the selection step 126.

Figure 6:
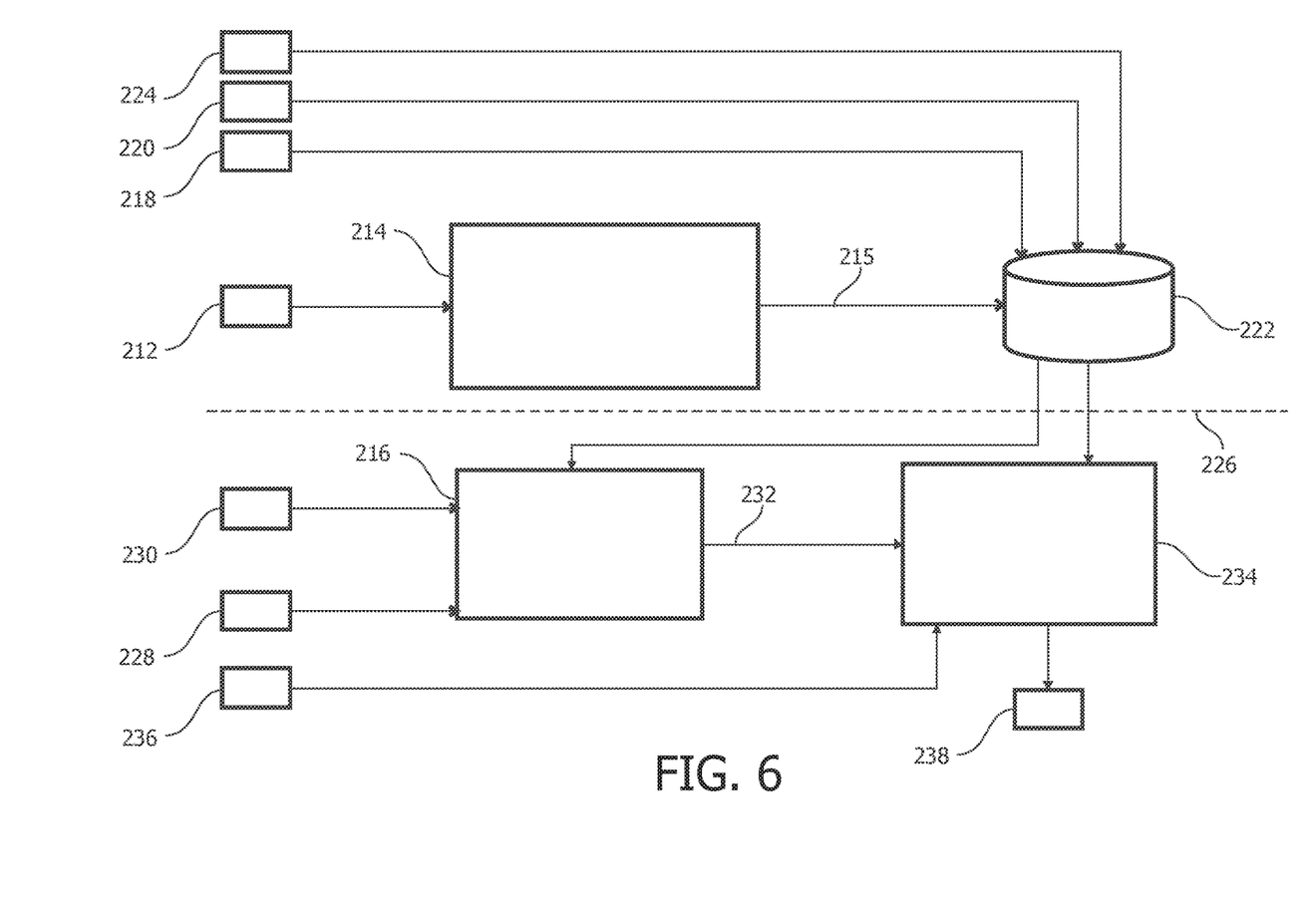
FIG. 6 shows a further exemplary embodiment of a method scheme according to an embodiment of the invention.

With reference to FIG. 6, a further example of a method according to the invention will be described. In a first acquisition step 212, first sequence of X-ray images is acquired, for example as angiography images. Then, in a determining step 214, optimal absorption means positions are determined or computed for each of the images of the first sequence of images acquired in acquisition step 212, indicated by an arrow from reference numeral 212 to 214. For instance, this computation can be based on a fuzzy segmentation of the vascular structure acquired in the angiography images. Thus, absorption means positions, for example wedge positions 215 are provided. Further, for being able to associate images of a second sequence of X-ray images in an association step 216 with corresponding images of the first sequence of X-ray images, angulation data 218, and system information 220 is provided and linked to the respective wedge positions 215 of the images of the first sequence in an information attachment step 222.

Additionally, vascular information, for instance user given or computed on behalf of the acquired images of the first sequence, can also be provided as vascular information data 224 for the information attachment step 222.

The input of angulation data 218, of system information 220 and information data 224 for the information attachment step 222 is each indicated with an arrow from the respective boxes to the container-shaped information attachment step 222.

A separating line 226 separates the schematic drawing into an upper first part and a lower second part.

For example, the first upper portion can be a so-called angiography phase, whereas the lower second portion can be referred to as a fluoroscopy phase in case the first sequence of images is acquired by angiography and the second sequence of images is by fluoroscopy.

In the already mentioned association step 216, images of a second sequence of X-ray images, for example fluoroscopy images, are associated with corresponding images of the first sequence of images, for example angiography images. For this association 216, information is provided from the attachment step 222, indicated by a connecting arrow. For example, angulation data, system information, vascular information etc. can be provided. For association of the two respective sequences, further information for the second sequence is provided, for example angulation data 228, input into the association step 216. Additionally, also image content information, such as cardiovascular information, which can be user given or image based generated, can also be provided as additional data 230, which input into association step 216 is also indicated with an arrow.

Since in the attachment step 222, also optimal position data for the position of the absorption means is provided to the association step 216, in combination with the additional data 230 and the angulation data 228, wedge or absorption means position data 232 is provided, indicated as an arrow leaving the box of the association step 216.

As an example, in a further alignment step 234, a geometrical alignment between the second sequence and the first sequence is provided. Therefore, system information from the upper half, i.e. system information referring to the acquisition of the first sequence of images in the acquisition step 212, is brought into relation with system information 236, indicated with an arrow entering the alignment step 234, derived from the acquisition system for the second sequence. Thus, it is possible to provide aligned absorption means position data 238 as an output from the alignment step 234.

With reference to an example where a first sequence of images is derived by angiography and a second sequence of images is derived by fluoroscopy, some aspects of the invention shall be described further. For the optimal absorption means position in angiography, in a first stage, the angiographies are analyzed and the optimal wedge positions corresponding to the specific branch imaged under the specific angulation are established. To do so, for example, it is possible to rely on a fuzzy segmentation of the contrasted vessels during the angiography. This, for example, would allow defining the vasculature of interest.

The optimal position would be the one that covers the largest part of the image while leaving the whole vasculature of interest uncovered. This wedge position, or absorption means position, can also incorporate safety margins, taking into account different breathing depths between angiography and fluoroscopy.

For the fluoroscopy/angiography correspondence, each fluoroscopy is associated with a previous angiography corresponding to the same branch imaged under the same angulation. To establish that correspondence, for example, two pieces of information are provided: First, the imaging angulation which is directly provided by the system. Second, the type of vasculature that is imaged (in practice, right or left coronary artery). This information could be given by the user or can automatically be computed from the image. More than one angiography run could be selected that way. As already indicated above, different strategies to select the best of them are possible, for example the last one, the one that was injected the most, depending on fuzzy segmentation, the one that gives the absorption means positions that cover the most or the less the image, etc.

As an additional step, an alignment can take place of the fluoroscopy images and the selected angiography, which alignment can also be referred to as a geometrical alignment. This alignment step uses information from the system to account for possible modifications of the relative position of the imaging system and patient, between the selected angiography and the considered fluoroscopy. Those pieces of information may include the table position that allows to compensate for a possible table panning, the selected field of view, that allows to correct for a possible zooming, the distance of patient and detector, that allows to correct for a possible zooming, etc.

According to a further example, an even finer spatial alignment can be computed on behalf of an acquired first image of the second sequence. The computed adjustment of the alignment can then be applied for the acquisition of further images of the second sequence.

According to an exemplary embodiment, the alignment is fine-tuned during the second sequence by a tuning computation every x images, i.e. in predetermined intervals.

According to a further example, the absorption means positions, for example wedge positions, from the selected angiography are used during the fluoroscopy, for example once they are compensated for translational motion and zooming. They are optimal in the sense that they cover as much as possible while leaving the vasculature, in which the clinician will navigate, uncovered.

According to a further example, no image processing is needed during fluoroscopy. Therefore, the fluoroscopy absorption means or wedge positions can be set as soon as the user begins the fluoroscopy and the absorption means, respectively the wedges, are positioned accordingly.

According to another aspect of the invention, a first image of the second sequence of images is used for determining the vasculature by image processing. For example, thus it is possible to determining whether the interventional device is in the right or left part of a two part vasculature structure, such as the coronary tree structure. In such a case, the optimal absorption means or wedge positions are set in the very beginning of the fluoroscopy as well and the absorption means can be positioned immediately before proceeding with the second sequence of images.

Figure 8:
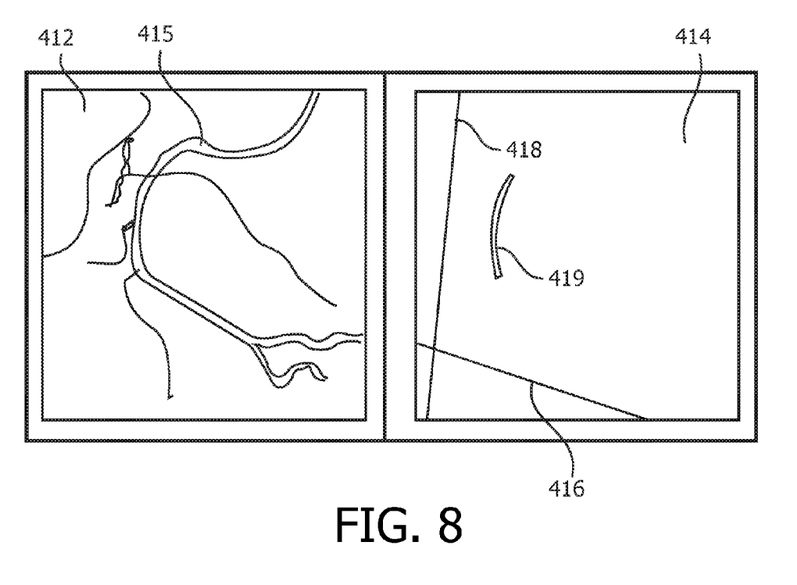
FIG. 8 schematically shows another example of an image of a first sequence and an image of a second sequence with indicated determined optimal positions for an X-ray absorption means according to another exemplary embodiment.
Figure 9:
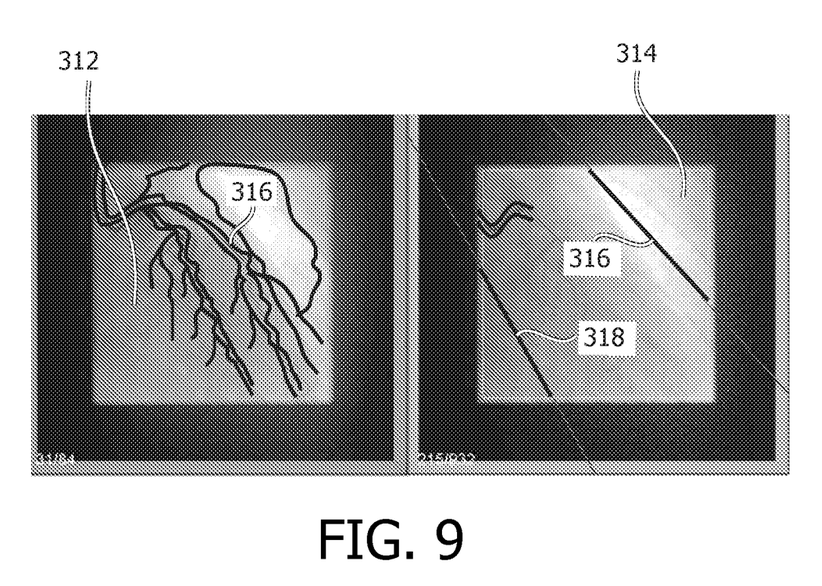
FIGS. 9 and 10 show photographic images of the examples shown in FIGS. 7 and 8.
Figure 10:
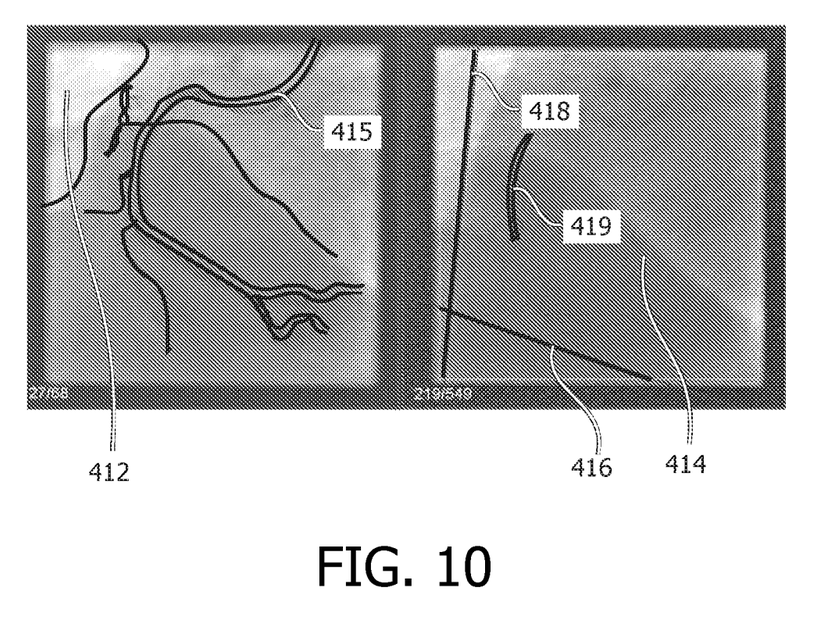

In the following, FIGS. 7 and 8 as well as their respective photographic images in FIGS. 9 and 10, are described in order to explain further aspects of the invention.

Figure 7:
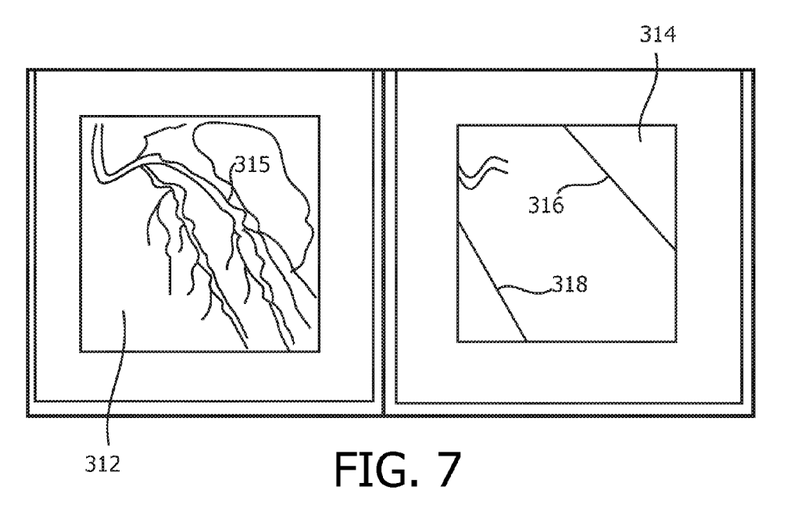
FIG. 7 schematically shows an image of a first sequence of images and an image of a second sequence of images with indicated determined optimal positions for X-ray absorption means according to an exemplary embodiment of the invention.

In the left part of FIG. 7, an image 312 of a first sequence of images is shown, whereas in the right part, a corresponding second image 314 of a second sequence of images is shown. As an example, the first image 312 of the first sequence has been acquired as an angiography image, thus showing, just as an example, a vessel structure. The right part is showing the corresponding image of the second sequence acquired as a fluoroscopy image. The first image shown in the left part is used for computing of optimal absorption means positions, for example, optimal wedges positions, which are then associated or transformed respectively to the second image. This position computing is done on image content shown in the left image, for example a visible vessel structure 315. As an example, two computed wedge positions 316 and 318 are indicated by a thin line. For example, the wedge positions that actually touch the image borders, are covered, that is not shown. The vessel structure can hardly be seen in the right part of FIG. 7.

As an example, FIG. 7 shows the left coronary tree, whereas FIG. 8 shows an example for a right coronary tree.

The left part shows a first image 412, whereas the right part shows a second image 414. The first image 412 belongs to a first sequence of images, for example angiography images where a vessel structure 415 can be seen. The second image 414 relates to a second sequence of images, for example acquired as fluoroscopy images. Here, the vessel structure cannot be identified anymore, only a device 419 can be seen.

According to one example, as can be seen from FIG. 7 and FIG. 8, as well as from FIGS. 9 and 10, the first sequence of images provides such image information that the region of interest can easily be determined, for example by computational analysis of the image content shown. Simply said, in these images it is possible to detect the vessel structure and thus determine a region of interest. Hence, positions for absorption means can then be computed. The computation of such positions is not possible for the right halves, since these images of the second sequence show only rare vessel structure information due to different acquisition modes, i.e. the absence (FIG. 8) or little amount (FIG. 7) of contrast agent, for example. But since the association of the first and the second sequence images is possible due to image data, the computed positions for the absorption means can then be transferred to the second sequence of images, also indicated in the right half of FIG. 8 by two lines 416 and 418.

FIGS. 9 and 10 show the respective photographic images with overlaid lines indicating the positioning for absorption means for a better understanding.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

The invention claimed is:

1. A device for automatic absorption device positioning in X-ray image acquisition, comprising:
   a processing unit; and
   a control device coupled to the processing unit and configured to control a position of an imaging device, wherein the processing unit is adapted to:
   i) receive image data of images of a first sequence of sequentially exposed X-ray images of an object;
   ii) determine optimal position for an X-ray absorption device for each of the images of the first sequence of X-ray images, wherein at least two of the first sequence of X-ray images have different corresponding determined optimal positions;
   iii) associate images of a second sequence of X-ray images with corresponding images of the first sequence of X-ray images by establishing a correspondence for the first sequence of X-ray images and the second sequence of X-ray images based on an imaging angulation and a type of vasculature being imaged; and
   iv) select the determined optimal position for the X-ray absorption device of the associated corresponding images of the first sequence of X-ray images for an acquisition of the second sequence of X-ray images, wherein at least two of the second sequence of X-ray images correspond to the at least two of the first sequence of X-ray images,
   wherein the control device is configured to receive the selected optimal positions for the second sequence of X-ray images and is configured to position the imaging device during the second sequence of X-ray images.

2. A method for automatic absorption device positioning in X-ray image acquisition, comprising acts of:
   a) acquiring image data of images of a first sequence of X-ray images of an object;
   b) determining, for each of the images of the first sequence of X-ray images, optimal position for an X-ray absorption device, wherein at least two of the first sequence of X-ray images have different corresponding determined optimal positions;
   c) associating images of a second sequence of X-ray images with corresponding images of the first sequence of X-ray images by establishing a correspondence for the first sequence of X-ray images and the second sequence of X-ray images based on an imaging angulation and a type of vasculature being imaged;
   d) selecting the determined optimal position of the associated corresponding images of the first sequence of X-ray images for an acquisition of the second sequence of X-ray images, wherein at least two of the second sequence of X-ray images correspond to the at least two of the first sequence of X-ray images.

3. The method according to claim 2, comprising acts of acquiring of the second sequence of X-ray images, wherein the determined optimal positions are selected during or prior to the acquisition of the second sequence of X-ray images, and positioning the X-ray absorption device according to the selected determined optimal positions.

4. The method according to claim 2, wherein the images of the first sequence of X-ray images and the images of the second sequence of X-ray images are acquired according to at least one different image acquisition parameter.

5. The method according to claim 4, wherein the at least one image acquisition parameter comprises image contrast and wherein the images of the first sequence of X-ray images are acquired with a higher image contrast agent than the images of the second sequence of X-ray images.

6. The method according to claim 2, wherein act c) comprises spatially aligning images from among the corresponding images of the first sequence of X-ray images with the associated images of the second sequence of X-ray images; and wherein the respective selected optimal positions are adjusted according to their respective alignments.

7. The method according to claim 6, wherein for the alignment, system information is used to account for possible modifications of a relative position of an imaging system and the object of interest between the acquisition of the images of the first sequence of X-ray images and the acquisition of the second sequence of X-ray images.

8. A non-transitory computer readable medium for automatic X-ray absorption-device positioning, the medium embodying a program having instructions executable by a processor for performing a plurality of acts, among the plurality there being the acts of:
   a) acquiring image data of images of a first sequence of X-ray images of an object;
   b) determining, for each of the images of the first sequence of X-ray images, optimal position for an X-ray absorption device, wherein at least two of the first sequence of X-ray images have different corresponding determined optimal positions;
   c) associating images of a second sequence of X-ray images with corresponding images of the first sequence of X-ray images by establishing a correspondence for the first sequence of X-ray images and the second sequence of X-ray images based on an imaging angulation and a type of vasculature being imaged; and
   d) selecting the determined optimal position of the associated corresponding images of the first sequence of X-ray images for an acquisition of the second sequence of X-ray images, wherein at least two of the second sequence of X-ray images correspond to the at least two of the first sequence of X-ray images.

9. An apparatus for automatic absorption device positioning in X-ray image acquisition, comprising:
   a processing unit wherein the processing unit is adapted to:
   i) receive image data of images of a first sequence of X-ray images of an object;
   ii) determine optimal position of an X-ray absorption device for each of the images of the first sequence of X-ray images, wherein at least two of the first sequence of X-ray images have different corresponding determined optimal positions;
   iii) associate images of a second sequence of X-ray images with corresponding images of the first sequence of X-ray images by establishing a correspondence for the first sequence of X-ray images and the second sequence of X-ray images based on an imaging angulation and a type of vasculature being imaged; and
   iv) select, for an acquisition of the second sequence of X-ray images, the determined optimal positions for the associated corresponding images of the first sequence of X-ray images, wherein at least two of the second sequence of X-ray images correspond to the at least two of the first sequence of X-ray images.

10. A medical imaging system comprising the apparatus of according to claim 9, further comprising an X-ray source, and an X-ray detector that are adapted to acquire the images of the first sequence of X-ray images with a higher image contrast agent than the images of the second sequence of X-ray images.

11. The apparatus of claim 9, the act ii) preceding, for a plurality of images from among the first sequence of X-ray images, the act iv).

12. The apparatus of claim 11, the plurality comprising all of the images of the first sequence of X-ray images.

13. The method of claim 2, the act b) preceding, for a plurality of images from among the first sequence of X-ray images, the act d).

14. The method of claim 13, the plurality comprising all of the images of the first sequence of X-ray images.

15. The computer readable medium of claim 8, the act b) preceding, for a plurality of images from among the first sequence of X-ray images, the act d).

16. The computer readable medium of claim 15, the plurality comprising all of the images of the first sequence of X-ray images.

17. The apparatus of claim 9, further comprising the X-ray absorption device.

18. The apparatus of claim 9, the processing unit being further adapted to, via the acts i), ii), and iii), generate a situation-specific database that includes optimized absorption device positions for respective images of the second sequence of X-ray images.

19. The apparatus of claim 9, the X-ray absorption device comprising: a) an X-ray diaphragm, b) a wedge, c) shutters, or d) any combination of one or more of a), b), and c).

20. A medical imaging system comprising:
   an X-ray source;
   an X-ray detector; and
   the apparatus according to claim 17;
   wherein the source and the detector are adapted to acquire image data of images of the first sequence of X-ray images and to acquire image data of images of the second sequence of X-ray images, the X-ray images of which are images of the object;
   wherein the X-ray absorption device is arranged between the source and the detector such that the object is placeable at least partially between the X-ray absorption device and the X-ray detector; and wherein a control is provided to position the X-ray absorption device; and
   wherein the processing unit activates the control according to the determined optimal position for the acquisition of the image data of the images of the second sequence of X-ray images.

* * * * *